US008283171B2

(12) United States Patent
Vankov et al.

(10) Patent No.: US 8,283,171 B2
(45) Date of Patent: *Oct. 9, 2012

(54) METHOD AND APPARATUS FOR AVALANCHE-MEDIATED TRANSFER OF AGENTS INTO CELLS

(75) Inventors: Alexander Vankov, Menlo Park, CA (US); Thomas W. Chalberg, Redwood City, CA (US); Philip Huie, Jr., Cupertino, CA (US); Daniel V. Palanker, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,934

(22) Filed: Mar. 8, 2011

(65) Prior Publication Data
US 2011/0229952 A1 Sep. 22, 2011

Related U.S. Application Data

(63) Continuation of application No. 11/526,153, filed on Sep. 22, 2006, now Pat. No. 7,923,251, which is a continuation-in-part of application No. 11/360,984, filed on Feb. 22, 2006, application No. 13/042,934, which is a continuation-in-part of application No. 11/505,249, filed on Aug. 15, 2006, now Pat. No. 8,101,169.

(60) Provisional application No. 60/655,559, filed on Feb. 23, 2005, provisional application No. 60/708,486, filed on Aug. 15, 2005.

(51) Int. Cl.
*C12N 15/87* (2006.01)
*C12N 13/00* (2006.01)
(52) U.S. Cl. ...... 435/461; 435/470; 435/471; 435/173.6
(58) Field of Classification Search .................... None
See application file for complete search history.

(56) References Cited

U.S. PATENT DOCUMENTS

| | | |
|---|---|---|
| 5,019,034 A | 5/1991 | Weaver et al. |
| 5,028,597 A | 7/1991 | Kodama et al. |
| 5,128,257 A | 7/1992 | Baer |
| 5,304,486 A | 4/1994 | Chang |
| 5,318,514 A | 6/1994 | Hofmann |
| 5,389,069 A | 2/1995 | Weaver |
| 5,468,223 A | 11/1995 | Mir |
| 5,665,567 A | 9/1997 | Eichner et al. |
| 5,688,233 A | 11/1997 | Hofmann et al. |
| 5,749,847 A | 5/1998 | Zewert et al. |
| 5,964,726 A | 10/1999 | Korenstein et al. |
| 6,267,954 B1 | 7/2001 | Abitbol et al. |
| 6,352,535 B1 | 3/2002 | Lewis et al. |
| 6,384,301 B1 | 5/2002 | Martinell et al. |
| 6,500,449 B2 | 12/2002 | Abitbol et al. |
| 6,521,430 B1 | 2/2003 | Orwar et al. |
| 6,528,315 B2 | 3/2003 | Bureau et al. |
| 6,593,130 B1 | 7/2003 | Sen et al. |
| 6,627,421 B1 | 9/2003 | Unger et al. |
| 6,632,672 B2 | 10/2003 | Calos |
| 6,663,894 B2 | 12/2003 | Abitbol et al. |
| 6,678,558 B1 | 1/2004 | Dimmer et al. |
| 6,780,178 B2 | 8/2004 | Palanker et al. |
| 6,800,484 B2 | 10/2004 | Nolan et al. |
| 6,808,925 B2 | 10/2004 | Calos |
| 6,939,862 B2 | 9/2005 | Bureau et al. |
| 7,109,034 B2 | 9/2006 | Orwar et al. |
| 7,923,251 B2 * | 4/2011 | Vankov et al. ............... 435/461 |
| 2003/0087859 A1 | 5/2003 | Kochanek et al. |
| 2004/0193097 A1 | 9/2004 | Hofmann et al. |
| 2005/0064578 A1 | 3/2005 | Muller-Hartmann et al. |
| 2005/0171039 A1 | 8/2005 | McSwiggen et al. |
| 2006/0115888 A1 | 6/2006 | Gamelin et al. |
| 2006/0123248 A1 | 6/2006 | Porter et al. |
| 2006/0269531 A1 | 11/2006 | Beebe et al. |

OTHER PUBLICATIONS

Borras, "Recent developments in ocular gene therapy," Experimental Eye Research, 76(6): 643-652 (2003).
Chalberg et al., "phiC31 integrase confers genomic integration and long-term transgene expression in rat retina," Investigative Ophthalmology & Visual Science, 46(6):2140-2146 (2005).
Miller et al., "Precision and safety of the pulsed electron avalanche knife in vitreoretinal surgery," Archives of Ophthalmology, 121(6):871-877 (2003).
Semkova et al., "Autologous transplantation of genetically modified iris pigment epithelial cells: a promising concept for the treatment of age-related macular degeneration and other disorders of the eye," PNAS 99(20):13090-13095 (2002).
Tamai, "Progress in pathogenesis and therapeutic research in retinitis pigmentosa and age-related macular degeneration," Nippon Ganka Gakkai Zasshi, 108(12): 750-751 (2004). (English translation of abstract submitted).
Chalberg et al., "Novel Physical Methods for Nonviral DNA Transfer to Rabbit Retina," Molecular Therapy, 11(1):5299 Abstract 770 (2005).
Hageman et al., "A common haplotype in the complement regulatory gene factor H (HF1/CFH) predisposes individuals to age-related macular degeneration," PNAS 102(20):7227-7232 (2005).
Lai et al., "Long-Term Evaluation of AAV-Mediated sFlt-1 Gene Therapy for Ocular Neovascularization in Mice and Monkeys," Mol. Therapy 12(4): 659-668 (2005).
Mohan et al, "Gene Therapy in the Cornea," Progress in Retinal and Eye Research 24:537-559 (2005).
Kumar-Singh et al, "Barriers for Retinal Gene Therapy: Separating Fact From Fiction," Vision Research 48: 1671-1680 (2008).

(Continued)

*Primary Examiner* — Jim Ketter
(74) *Attorney, Agent, or Firm* — Ann-Louise Kerner; K&L Gates LLP

(57) ABSTRACT

The present invention provides a method and apparatus for transferring an agent into a cell. The method includes the steps of providing an agent outside of a cell and generating a vapor bubble and a plasma discharge between an avalanche electrode and a conductive fluid surrounding the cell. The vapor bubble and plasma discharge generate a mechanical stress wave and an electric field, respectively. The combination of this mechanical stress wave and electric field results in permeabilization of the cell, which in turn results in transfer of the agent into the cell.

17 Claims, 15 Drawing Sheets

OTHER PUBLICATIONS

Lund et al, "Retinal Transplantation: Progress and Problems in Clinical Application," J. Leukoc. Biol., 74: 151-160, 2003).

Palanker, et al, "Pulsed Electron Avalanche Knife (PEAK) for Intraocular Surgery," Investigative Opthalmology & Virtual Sci., 42(11):2673-2678 (2001).

International Search Report issued for PCT/US06/32249, dated Mar. 2, 2010 (1 page).

International Search Report issued for PCT/US06/37010 dated Aug. 5, 2008 (1 page).

* cited by examiner

A

B

METHOD AND APPARATUS FOR AVALANCHE-MEDIATED TRANSFER OF AGENTS INTO CELLS

CROSS-REFERENCE TO RELATED APPLICATIONS

This application is a continuation of U.S. application Ser. No. 11/526,153, filed Sep. 22, 2006 now U.S. Pat. No. 7,923, 251, which is a continuation-in-part of U.S. application Ser. No. 11/360,984, filed Feb. 22, 2006,which claims priority to U.S. Provisional Application No. 60/655,559, filed Feb. 23, 2005; and this application is a continuation-in-part of U.S. application Ser. No. 11/505,249, filed Aug. 15, 2006 now U.S. Pat. No. 8,101,169, which claims priority to U.S. Provisional Application No. 60/708,486, filed Aug. 15, 2005.

STATEMENT REGARDING FEDERALLY SPONSORED RESEARCH OR DEVELOPMENT

This invention was made with Government support under contract FA9950-04-1-0075 awarded by the Air Force Office of Scientific Research and under contracts HL068112 and EY012888 awarded by the National Institutes of Health. The Government has certain rights in this invention.

FIELD OF THE INVENTION

The present invention relates generally to cellular and molecular biology. More particularly, the present invention relates to a method and apparatus for permeabilization of cellular membranes for transfer of agents into cells.

BACKGROUND

A wide variety of physical methods for delivery of drugs (or other materials) to biological cells are known, including injection, electroporation, sonophoresis, etc. Electroporation, which entails the formation of self-healing pores in a cellular membrane, is of considerable interest. A major reason for this interest is that electroporation tends to be more effective than chemical delivery methods. Accordingly, many variants of electroporation have been investigated, including combined use of sonophoresis and electroporation.

Physical approaches such as electroporation for delivery of naked DNA represent a promising and rapidly expanding field. "Molecular delivery" to cells using physical methods encompasses delivery of DNA, RNA, siRNA, oligonucleotides, proteins, as well as small molecules such as drugs or dyes. Electroporation has won wide support as a tool for DNA transfer and is the preferred non-viral method for many applications. In most protocols, cells are suspended in a cuvette, exposed to a train of electric pulses using plate electrodes to achieve a uniform electric field, and then returned to culture. The major advantage of electroporation is that it is, in theory, effective for nearly all cell types. Despite these advantages, high rates of cell death and difficulty with in situ methods remain problems for many applications. Accordingly, there is a need in the art to develop novel methods for transfer of DNA and other small molecules into biological cells.

SUMMARY OF THE INVENTION

The present invention provides a method and apparatus for transferring an agent into a cell. The method includes the steps of providing an agent outside of a cell and generating a vapor bubble and a plasma discharge between an avalanche electrode and a conductive fluid surrounding the cell. The vapor bubble and plasma discharge generate a mechanical stress wave and an electric field, respectively. The combination of this mechanical stress wave and electric field results in permeabilization of the cell, which in turn results in transfer of the agent into the cell.

In order to generate the vapor bubble and plasma discharge between the avalanche electrode and the conductive fluid, a non-uniform electric field is preferably generated between the avalanche electrode and a return electrode. The portion of the electric field around the avalanche electrode must be strong enough to generate the plasma discharge and the vapor bubble. Depending on the geometry of the electrodes, the electric field is preferably in the range of about 0.1 kV/cm to about 100 kV/cm. To achieve this electric field strength, a voltage of between about 100 V and about 10 kV may be applied to the avalanche electrode. This voltage may be applied as a monophasic pulse or a biphasic pulse. Pulse duration is preferably in the range of about 100 ns to about 1 ms. Between 1 and 100 voltage pulses may be applied to the avalanche electrode to generate the vapor bubble and plasma discharge. The voltage pulses may be applied with a frequency in the range of about 0.1 Hz to about 1 kHz.

According to the present invention, an agent may be transferred to any type of biological cell. Examples include prokaryotic cells, eukaryotic cells, primary cells, cell lines, and tissues. Similarly, any type of agent may be transferred into the cell. Examples include, but are not limited to, proteins, peptides, oligonucleotides, therapeutic agents, small molecules, DNA, RNA, and small interfering RNA (siRNA). In a preferred embodiment the agent is a plasmid DNA molecule. Such DNA molecules may contain cassettes that encode proteins or RNA molecules such as micro-RNA or short hairpin RNA.

The present invention also provides an apparatus for transferring an agent into a cell. The apparatus includes an avalanche electrode, a return electrode, a voltage source, and circuitry. The avalanche electrode is disposed near the cell and is made of a material of sufficiently high melting temperature to resist melting during plasma discharge. The voltage source provides a voltage between the avalanche electrode and the return electrode, which in turn generates a non-uniform electric field between the avalanche electrode and the return electrode. The voltage source must provide a voltage of sufficient strength such that the portion of the non-uniform electric field around the avalanche electrode is sufficient to generate a vapor bubble and plasma discharge between the avalanche electrode and a conductive medium surrounding the cell. Similarly, the circuitry, which connects the avalanche electrode, return electrode, and voltage source, must be capable of conducting current at a level sufficient to generate the vapor bubble and plasma discharge.

BRIEF DESCRIPTION OF THE FIGURES

The present invention together with its objectives and advantages will be understood by reading the following description in conjunction with the drawings, in which.

DETAILED DESCRIPTION OF THE INVENTION

Avalanche Method

Figure 1:
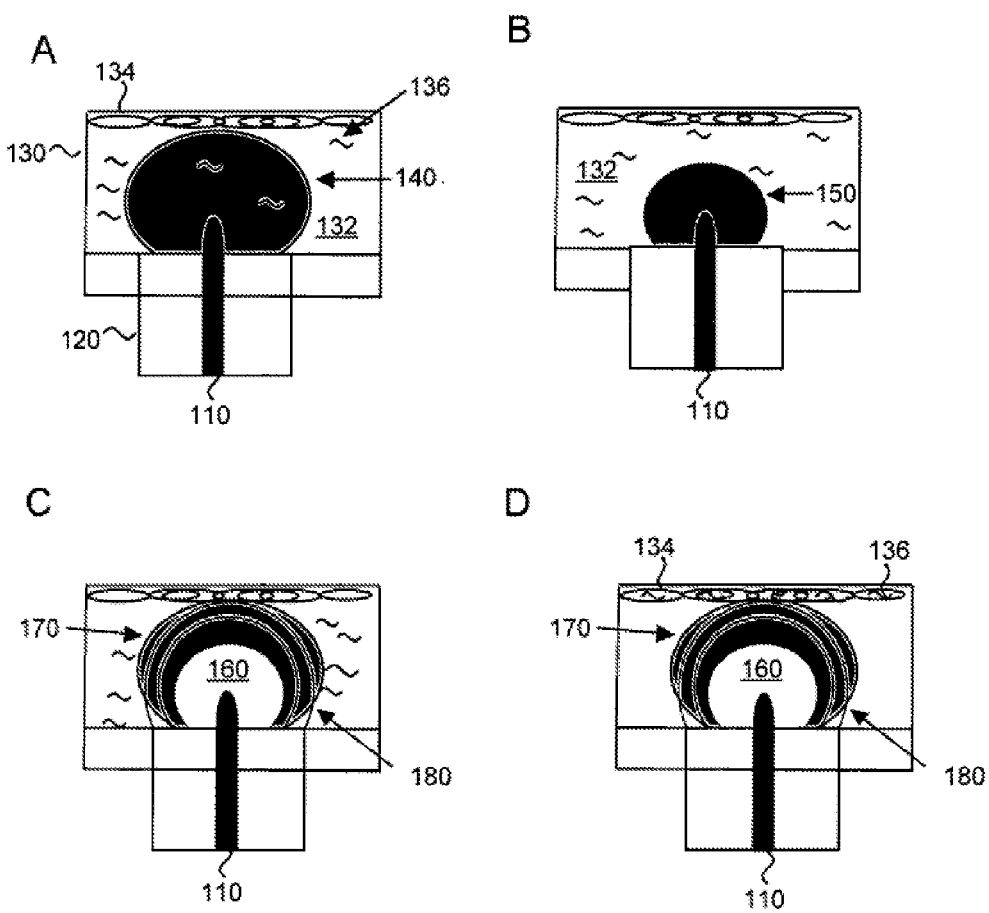
FIG. 1 shows the avalanche method according to the present invention.

The inventors have discovered that when sufficiently high voltage is applied to an electrode, a mechanical stress wave synchronized with a pulse of electric current can be produced and applied to cells. This in turn leads to permeabilization of the cells, which allows transfer of an agent that is external to the cells into the cells. FIG. 1A-C shows three stages that occur when a high voltage is applied to an electrode 110 covered by insulation 120. Electrode 110 is situated in tissue culture well 130, with conductive liquid medium 132, cells 134, and agent 136. (While cells are pictured in this figure, tissue could also be used). When a voltage is first applied to electrode 110, (FIG. 1A), an electric field 140 is generated around the un-insulated portion of electrode 110. If the electric field in the medium is sufficiently high, generated Joule heat leads to rapid vaporization of liquid medium 132 in the areas adjacent to electrode 110, resulting in generation of a vapor bubble 150 (FIG. 1B). As soon as vapor bubble 150 is formed, it disconnects the surface of electrode 110 from conductive medium 132, so that the electric current stops flowing, and the electric field on the target cells is terminated. To overcome this difficulty, the vapor in the bubble can be ionized to form ionized vapor 160, which restores the electrical conductivity, as shown in FIG. 1C. Ionized vapor 160, also known as plasma, forms a kind of virtual electrode with electric field 170. During this process, the formation of the vapor bubble, and its subsequent collapse, causes a propagating shock wave through the medium, exposing the cells or tissue to mechanical stress 180. The combination of the shock wave and the electric field leads to permeabilization of cells 132, such that agent 136 may enter cells 132 (FIG. 1D). Highlighting the role of the electron-avalanche in the plasma-Mediated electric discharge, the inventors have named this technique the avalanche method.

Figure 2:
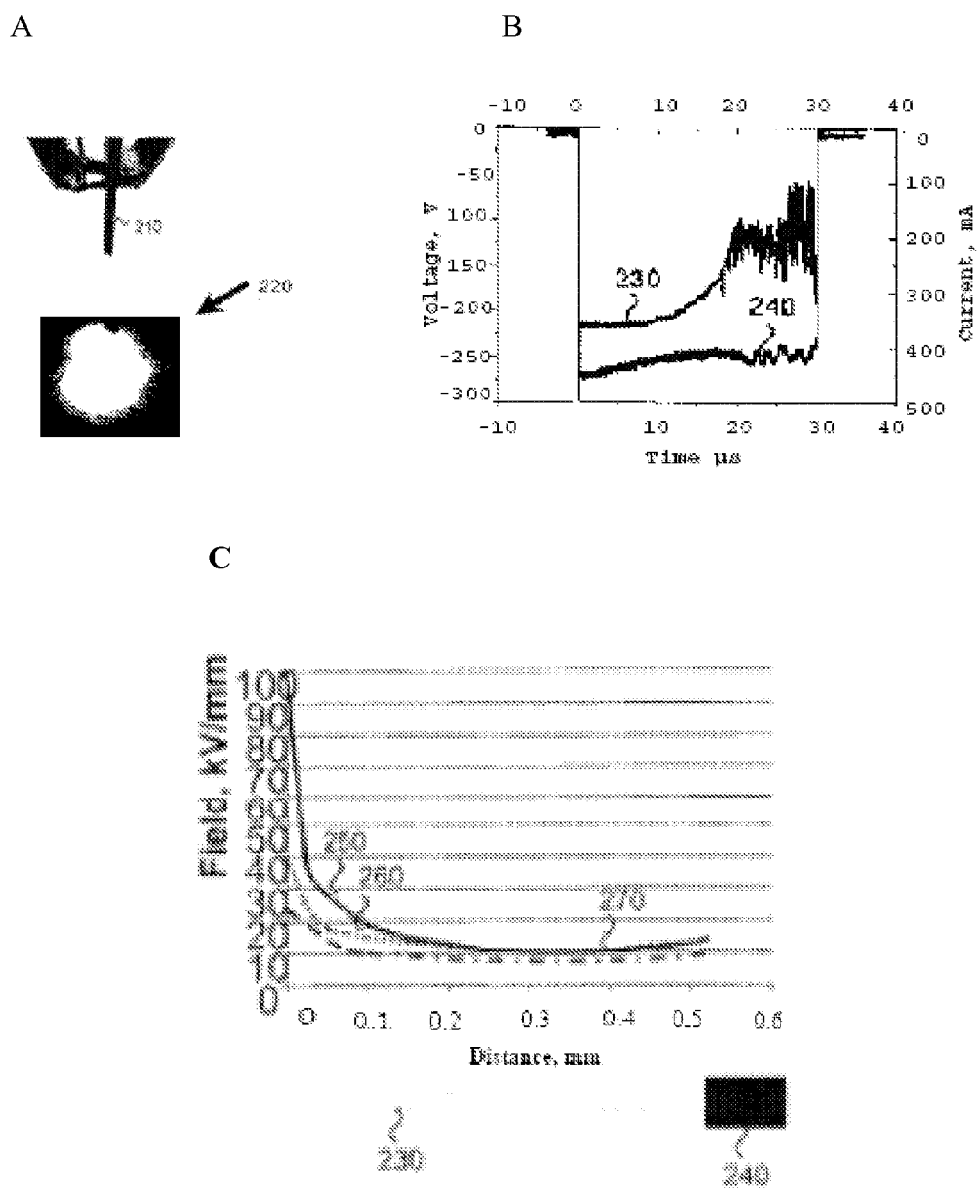
FIG. 2 shows the use of the avalanche method according to the present invention with wire electrodes.

The process described in FIG. 1 works when the electric field on the surface of the electrode is relatively uniform, or when the vapor bubble is larger than the electrode. Alternatively, electrodes with a very uneven electric field may be used, so that the vapor cavity formed at the apex does not cover the whole surface of the electrode with a lower electric field. This way the electric current to the medium will not be completely disconnected. One example of an electrode geometry with a non-uniform electric field is a cylindrical probe, such as a wire, with a sharp end. FIG. 2A shows an image of a wire electrode 210 producing a plasma discharge 220. As can be seen from FIG. 2A, the plasma discharge is clearly visible. It is also clearly audible. FIG. 2B shows current 230 and voltage 240 versus time when a voltage is applied to a wire probe. In this particular example, the wire probe was 50 µm in diameter and electrical pulses of up to 600 V were used to produce an electric field at the tip of the wire of about 30 kV/cm. However, these parameters may be varied. FIG. 2B shows that when a voltage is applied to such a probe, the initial 20 µs of the waveform exhibits reduction of the current due to beginning of vaporization. This is followed by stabilization of conductivity following ionization of the vapor cavity. The ionized vapor cavity serves as a transient electrode, which can greatly exceed the size of the probe, as shown in FIG. 2A. As a result, the distribution of the electric field becomes much more uniform than the one generated initially on the small wire electrode, thus leading to more uniform electroporation of the target cells or tissue.

FIG. 2C shows, for different diameters of electrodes, the field strength (kV/mm) along the length of electrode 230 covered by insulator 240. The electrode diameter indicated by the solid line 250 is 10 µm, the dotted line 260 is 25 µm, and the dashed line 270 is 50 µm. In this particular experiment, 600 V was applied to the electrode. FIG. 2C shows that for a cylindrical electrode with a sharp tip, there is a rapid decrease in electric field as one moves farther away from the tip of the electrode. Thus, the strength of the electric field at the apex of the electrode can be varied by changing the electrode diameter.

To produce a strong stress wave, the electric field on the electrode surface should be sufficient for rapid vaporization of the liquid medium. In addition, to maintain connectivity, the electric field should be high enough to induce ionization of the vapor. In this way, both a mechanical stress wave and an electric field can be synchronized, with maximal intensity at the surface of the electrode. In addition to these concerns, the plasma discharge must be controlled in order to maximize agent transfer efficiency and minimize cell death.

Several parameters may be varied to meet the above requirements, such as electric field strength, applied voltage, pulse duration, number of pulses, frequency, etc. The actual values of these parameters will depend on the specific electrode geometry. In general, however, applied voltages are preferably in the range of about 1 V to about 10 kV, more preferably between about 100 V and about 10 kV, most preferably between about 100 V and 1 kV. Applied voltage preferably results in an electric field between about 0.1 to about 100 kV/cm, more preferably about 10 to about 50 kV/cm, and most preferably about 30 kV/cm. Pulse duration is preferably in the range of about 1 ns to about 100 ms, more preferably between about 100 ns and about 1 ms. Either monophasic or biphasic pulses are suitable for the purposes of the present invention. However, biphasic pulses are preferred as they lead to less gas formation, nerve and muscle response, and electrode erosion. Any number of pulses may be used according to the present invention. The number of pulses is preferably between about 1 and 100, more preferably between about 1 and 50. When multiple pulses are used, the frequency of pulses should be in the range of about 0.1 Hz to about 1 kHz. Preferably, the frequency is less than about 1 kHz to prevent heat accumulation.

According to the present invention, an agent may be transferred to any type of biological cell. Examples include prokaryotic cells, eukaryotic cells, primary cells, cell lines, and tissues. Similarly, any type of agent may be transferred into the cell. Examples include, but are not limited to, proteins, peptides, oligonucleotides, therapeutic agents, dyes, small molecules, DNA, RNA, and small interfering RNA (siRNA). In a preferred embodiment the agent is a plasmid DNA molecule.

Avalanche Apparatus

Figure 3:
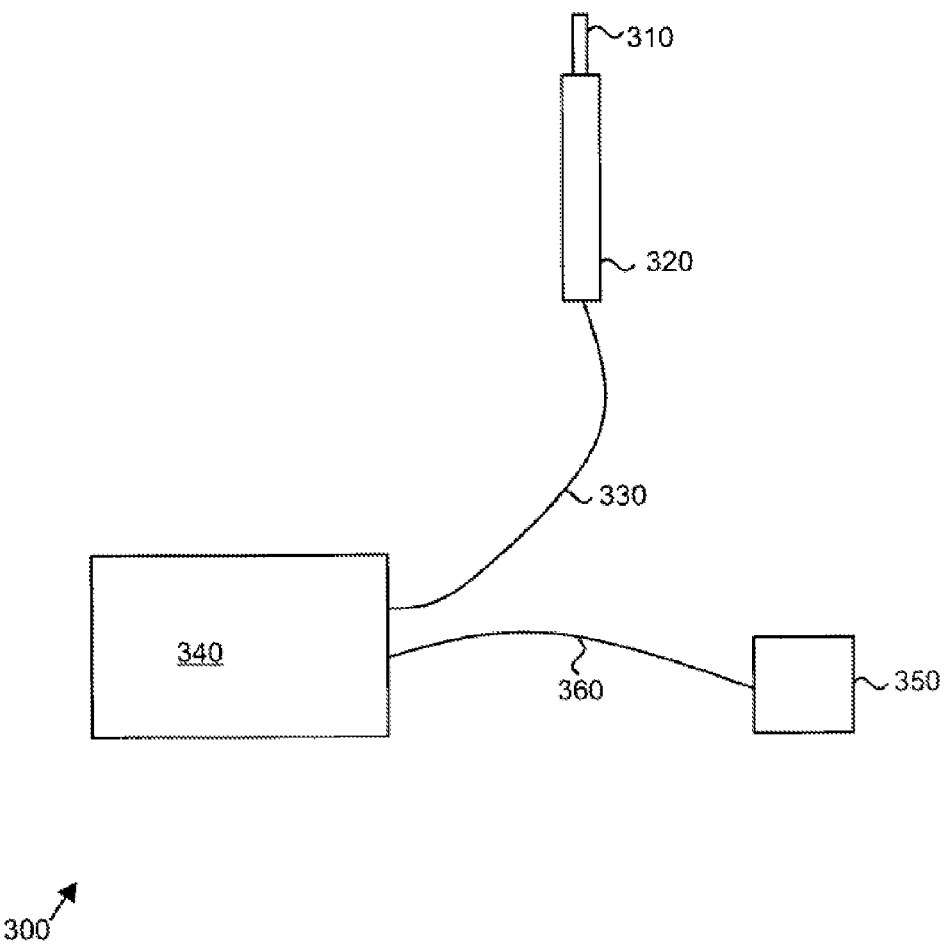
FIGS. 3-11 show examples of apparatuses according to the present invention.

An apparatus for performing the avalanche method according to the present invention, referred to hereafter as the avalanche apparatus, has several components, as shown in FIG. 3. The first component of avalanche apparatus 300 is avalanche electrode 310, so called because it is the electrode at which the vapor bubble and plasma discharge are generated. Avalanche electrode 310 is disposed near a cell (not shown) for which transfer of agent into the cell is desired. Preferably, avalanche electrode 310 is disposed between about 0.01 mm and about 1 cm from the cell, more preferably between about 0.1 mm and about 5 mm from the cell. Avalanche electrode 310 is partially covered by insulation 320. In one embodiment, insulation 320 covers all but the tip of avalanche electrode 310, to give greater spatial control of the generated vapor bubble and plasma discharge. Avalanche electrode 310 is preferably made of a material of sufficiently high melting temperature—exceeding about 1000 degrees C. and preferably about 2000 degrees C.—to resist melting during plasma discharge. Examples of such materials include, but are not limited to, titanium, molybdenum and titanium. Preferably, the width of avalanche electrode 310 is less than about 500 μm. Avalanche electrode 310 is connected to voltage source 340 through wire 330.

Avalanche apparatus 300 also includes a return electrode 350. Return electrode 350 is also connected to voltage source 340, for example through wire 360. Return electrode 350 and avalanche electrode 310 may be part of the same structure. For example, return electrode 350 may be situated at the base of insulation 320.

Voltage source 340 provides a voltage between avalanche electrode 310 and return electrode 350. Preferably, avalanche apparatus 300 is constructed such that voltage source 340 generates a non-uniform electric field between avalanche electrode 310 and return electrode 350, such that only the portion of the electric field around avalanche electrode 310 is of a strength sufficient to generate a vapor bubble and a plasma discharge between avalanche electrode 310 and a conductive medium surrounding the cell for which transfer of agent is desired. This may be accomplished by making the return electrode 350 larger than avalanche electrode 310. To maintain high electric field in the vicinity of the target cells, the return electrode 350 should be disposed father from the cell for which transfer of agent is desired relative to the avalanche electrode. Distance between the avalanche and return electrodes should not be smaller than about 0.01 mm, preferably not smaller than about 0.1 mm.

Preferably, the wires 330 and 360, as well as circuitry within voltage source 340, is capable of conducting voltage and current at a level sufficient to generate a vapor bubble and plasma discharge at avalanche electrode 310. The voltage should exceed the ionization threshold in water, which is on the order of about 200 V. For efficient generation of the rapidly expanding vapor bubble the pulse duration should not exceed the lifetime of the bubble. Lifetime of the sub-millimeter bubbles does not exceed 100 μs (Raleigh equation), so the rise time of the pulse of current should be in a microsecond range.

Avalanche apparatuses according to the present invention may include more than one avalanche electrode. In one embodiment, the avalanche apparatus includes a plurality of avalanche electrodes. These electrodes are preferably arranged in an array. The array may be one- or two-dimensional and may be of any shape, e.g. linear, square, rectangular, circular, etc. Preferably, the avalanche electrodes in the array are spaced between about 0.5 mm and about 2 cm apart. An array of return electrodes may also be used. In this case, the arrays of avalanche electrodes and return electrodes are preferably interleaved.

The avalanche electrode array may include a surface or substrate, where the avalanche electrodes either protrude from the surface or are planar to the surface. In one embodiment, the return electrode is also part of this surface. In this embodiment, the return electrode may be the entire surface or a portion of the surface. Alternatively, an array of return electrodes may protrude from or be planar to the surface.

Many embodiments of avalanche apparatuses are possible according to the present invention. The following is a discussion of several exemplary embodiments. Other embodiments are possible, and the following examples should in no way be construed as limiting.

Catheter Avalanche Apparatus

Figure 4:
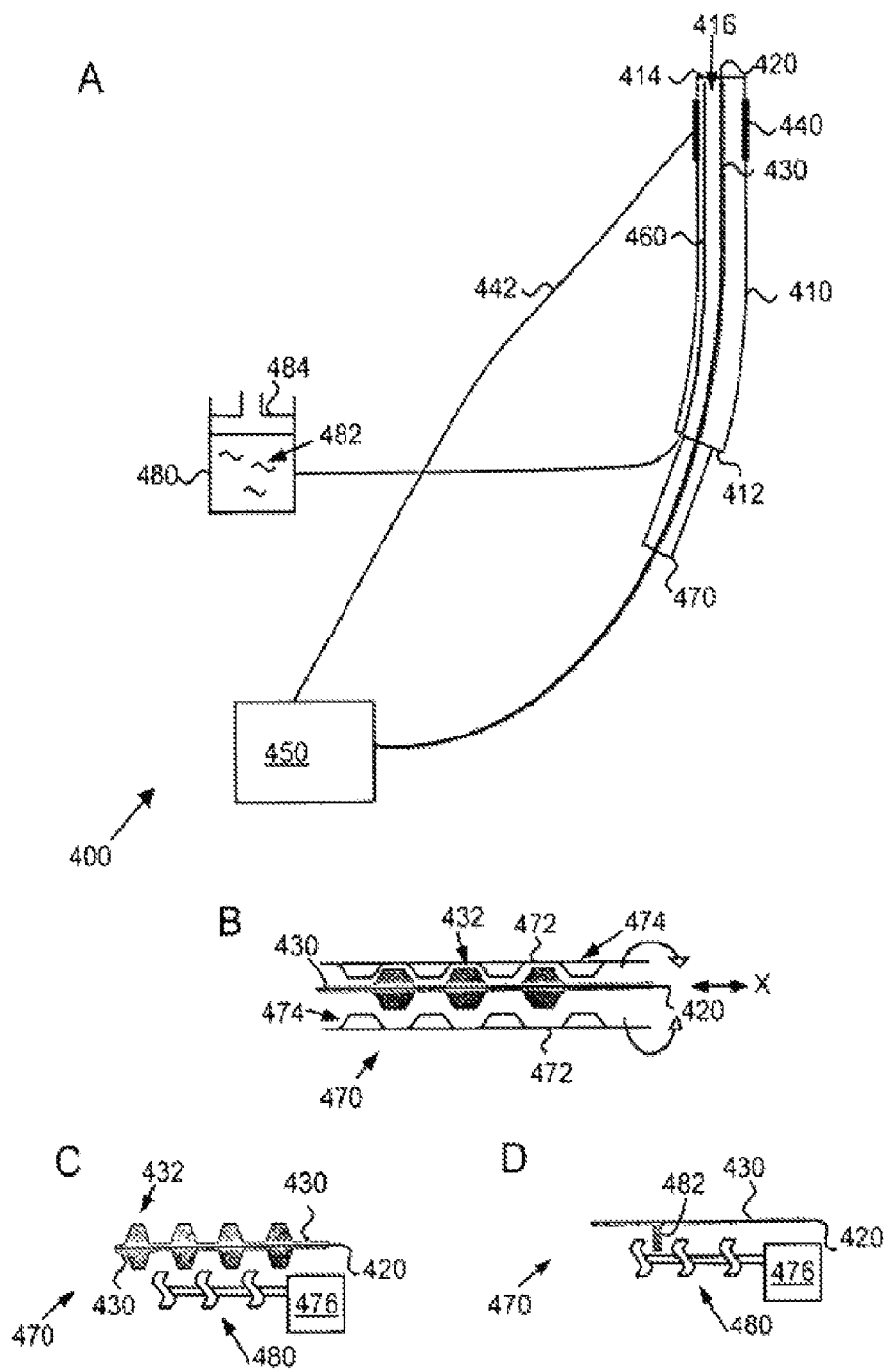

FIG. 4A illustrates an example of a catheter avalanche apparatus 400 according to the present invention. Catheter avalanche apparatus 400 may be useful for avalanche-mediated transfer of agents into blood vessels, cardiac muscle, or liver. Apparatus 400 includes a flexible sheath 410 with openings 412 and 414 and lumen 416. Lumen 416 contains avalanche electrode 420, which is insulated by insulation 430. Preferably, the un-insulated portion of avalanche electrode 420 protrudes a small amount out of opening 414. Preferably, the un-insulated portion of avalanche electrode 420 protrudes from about 1 mm to about 1 cm out opening 414. The insulated portion of avalanche electrode 420 may extend through opening 412 and connect to voltage source 450, as shown. Alternatively, avalanche electrode 420 may be connected to a wire that extends through opening 412 and connects to voltage source 450. Catheter avalanche apparatus 400 also includes a return electrode 440. Return electrode 440 may be, for example a ring of metal around flexible sheath 410. Return electrode 410 is connected to a second insulated wire 442, which is in turn connected to voltage source 450. In a preferred embodiment, catheter apparatus 400 also includes a source 480 of agent 482 for transferring into a cell. Source 480, which preferably contains a pump 484, is preferably connected to opening 414 through tubing 460, which enters sheath 410 through opening 412. Tubing 460 may be separate from avalanche electrode 420, as shown. Alternatively, tubing 460 may be attached to insulator 430, for example with glue; embedded in insulator 430; or surrounded by insulator 430, such that insulator 430 surrounds both tubing 460 and avalanche electrode 420.

In a preferred embodiment, the catheter avalanche apparatus 400 also includes retraction means 470, for retracting avalanche electrode 420 through opening 414 when it is not in use. Any retraction means may be used according to the present invention. Examples of three retraction means 470 are shown in FIG. 4B, C, and D. In FIG. 4B, avalanche electrode 420 is covered by insulation 430 having external threads 432. Avalanche electrode 420 and insulation 430 are surrounded by a sleeve 472 having internal threads 474. Internal threads 474 engage external threads 432, such that when sleeve 472 is turned relative to insulator 430 (as indicated by the curved arrows), insulator 474 and avalanche electrode 420 translate along the X-axis, as shown in the figure. Depending on the direction sleeve 472 is turned, insulator 430 and avalanche electrode 420 are either protracted or retracted. In FIG. 4C, avalanche electrode 420 is again covered by insulation 430 having external threads 432. However, in this case, translational movement is caused when threaded device 480 engages external threads 432. Preferably, threaded device 480 is powered by motor 476. The retraction means shown in FIG. 4C also uses threaded device 480. However, in this case, threaded device 480 engages pin 482 on insulation 430.

Syringe Avalanche Apparatus

Figure 5:
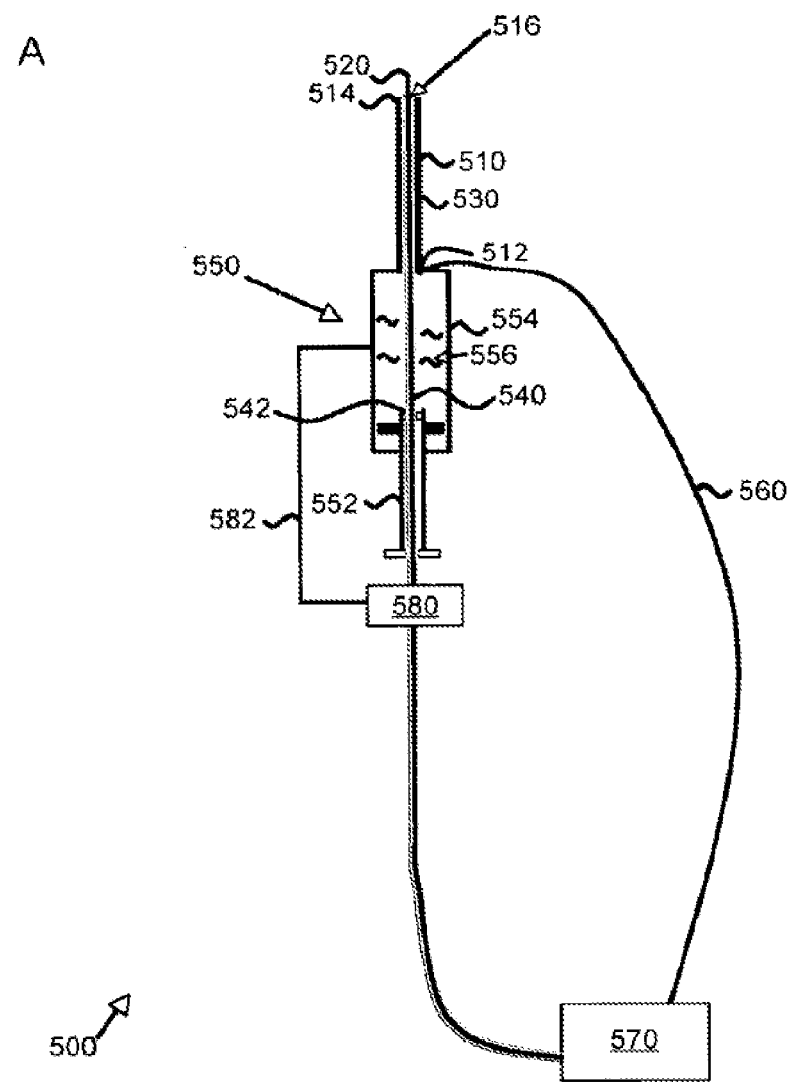
Figure 5:
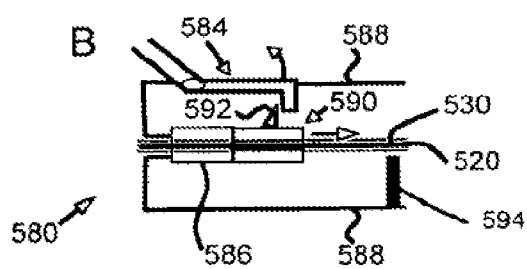

FIG. 5A illustrates an example of a syringe avalanche apparatus 500 according to the present invention. Syringe avalanche apparatus 500 may be useful for avalanche-mediated transfer of agents into muscle or skin. The syringe avalanche apparatus 500 contains a rigid sheath 510, e.g. a needle, with openings 512 and 514 and lumen 516. Preferably, rigid sheath 510 serves as a return electrode, and is connected to a voltage source 570 through wire 560. An avalanche electrode 520, covered by insulation 530, is situated inside lumen 516. Preferably, avalanche electrode 520 protrudes a small amount through opening 514. Preferably, the un-insulated portion of avalanche electrode 420 protrudes from about 1 mm to about 1 cm out of opening 514. Rigid sheath 510 is connected to syringe 550. Avalanche electrode 520 and insulation 530 extend through syringe 550 and connect to voltage source 570. Syringe 550 serves as a source 554 of agent 556 to be transferred into cells. Syringe 550 also includes a plunger 552 for expelling agent 556 from opening 514. Plunger 552 preferably includes O-rings 542, to prevent agent 556 from leaking out of syringe 550.

In a preferred embodiment, syringe 550 also includes a retraction means 580 for retracting avalanche electrode 520 into rigid sheath 510 when it is not in use. Retraction means 580 is preferably connected to source 554 through arm 582. Any retraction means may be used according to the present invention. In one aspect of this embodiment, retraction means 580 is a ballpoint pen mechanism. In another aspect of this embodiment, retraction means 580 is as shown in FIG. 5B. In this aspect, avalanche electrode 520, surrounded by insulation 530, is in turn surrounded by ring 590 with tooth 592. Ring 592 is connected to a spring 586, which is attached to a casing 588. A lever mechanism 584 is also attached to casing 588. When lever mechanism 584 engages tooth 592, spring 586 is compressed, and avalanche electrode 520 is retracted. When lever mechanism 584 is lifted, as indicated by the curved arrow, spring 586 decompresses, ring 592 stops against rod 594, and avalanche electrode 520 is pushed out through opening 514.

Probes With Avalanche Electrode Arrays

Figure 6:
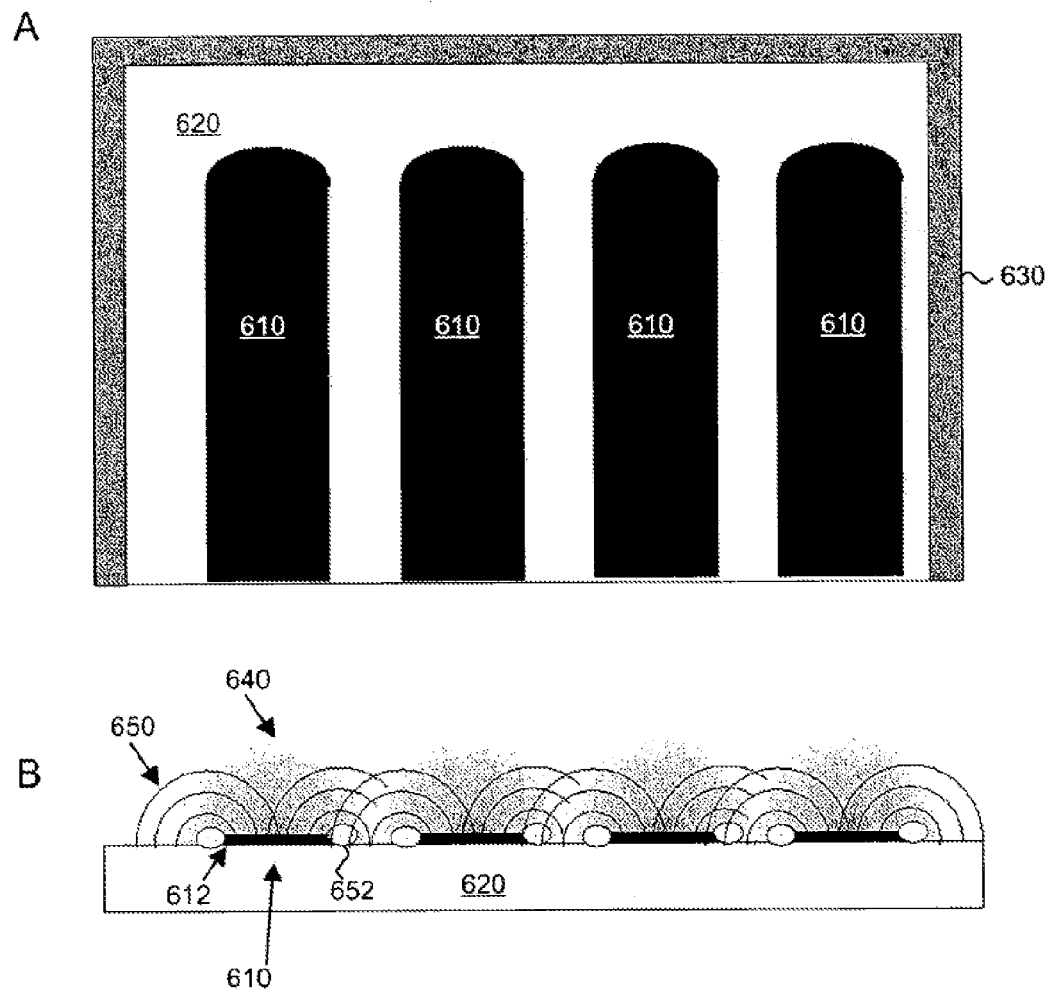

FIG. 6 shows a version of a probe in which an array of avalanche electrodes 610 are plated on a substrate 620. FIG. 6A shows a top view and FIG. 6B shows a side view of the probe. In this probe, substrate 620 is surrounded by return electrode 630. The pattern of avalanche electrodes 610 on substrate 620 forms the necessary proportion between electric field 640 and mechanical stress wave 650 due to plasma discharge 652. The probe in FIG. 6 has a singularity of the electric field 640 at the edges 612 of avalanche electrodes 610. Singularities serve as ignition points for plasma discharge 652 and generation of mechanical stress wave 650. In FIG. 1, plasma occupies the whole volume of the vapor cavity. In contrast, in FIG. 6, the electric field at the edges of the thin electrode is much higher than in front of its flat part so vaporization and ionization will occur (or start) primarily there. This implementation is simple and inexpensive, but it does not provide the flexibility to control mechanical and electric pulse parameters separately.

Figure 7:
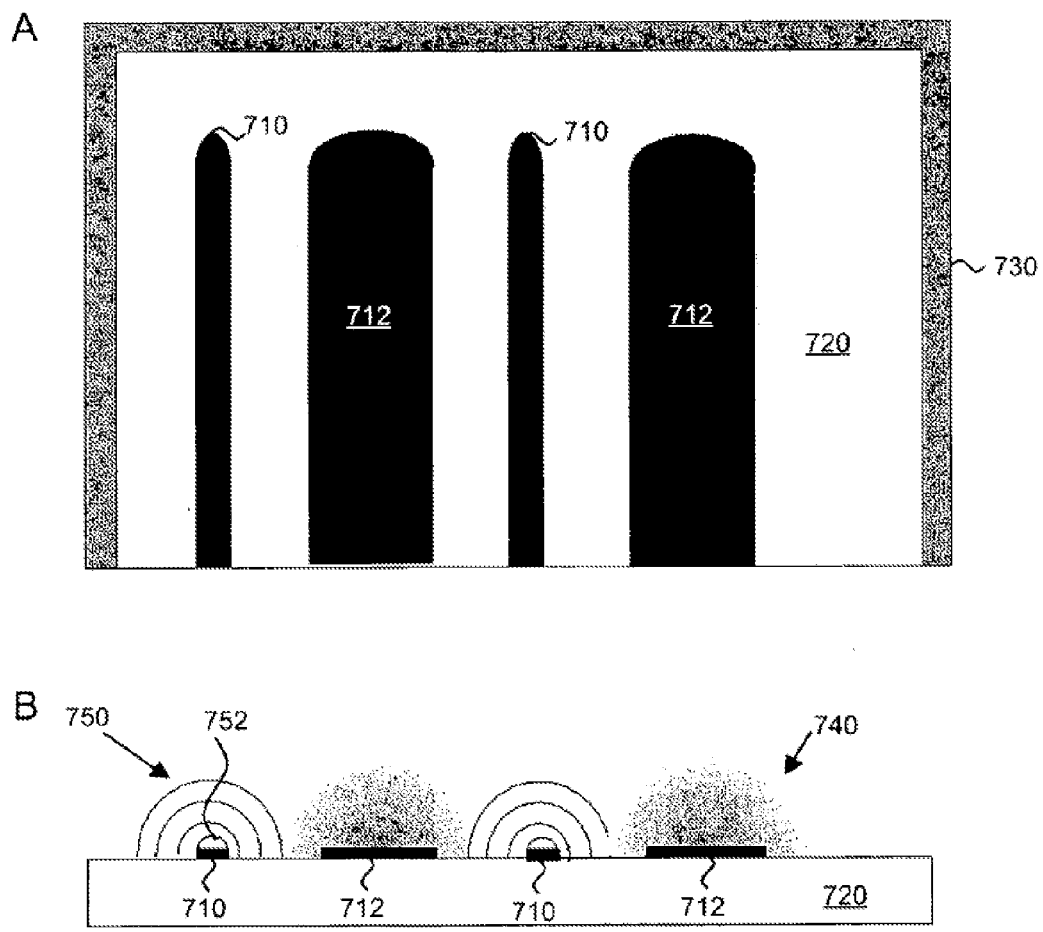

Another probe implementation, which allows separate control of mechanical stress wave 750 and electric field 740, is shown in FIG. 7. (FIG. 7A is a top view, FIG. 7B is a side view). In this implementation, two types of active electrodes, 710 and 712, are patterned on substrate 720, with return electrode 730 surrounding substrate 720. Electrodes 712 may be driven to generate an electric field 740, while electrodes 710 may be driven to generate plasma 752 and mechanical stress wave 750. (Plasma 752 also generates an accompanying electric field, not shown). Separate control of the amplitude of stress wave and electric field might be desirable for optimization of permeabilization. Generating them on the same electrode will make these values mutually dependent, while generation on two separate electrodes may provide independent control of these phenomena.

Avalanche Apparatus for Tissue Culture Plates

Figure 8:
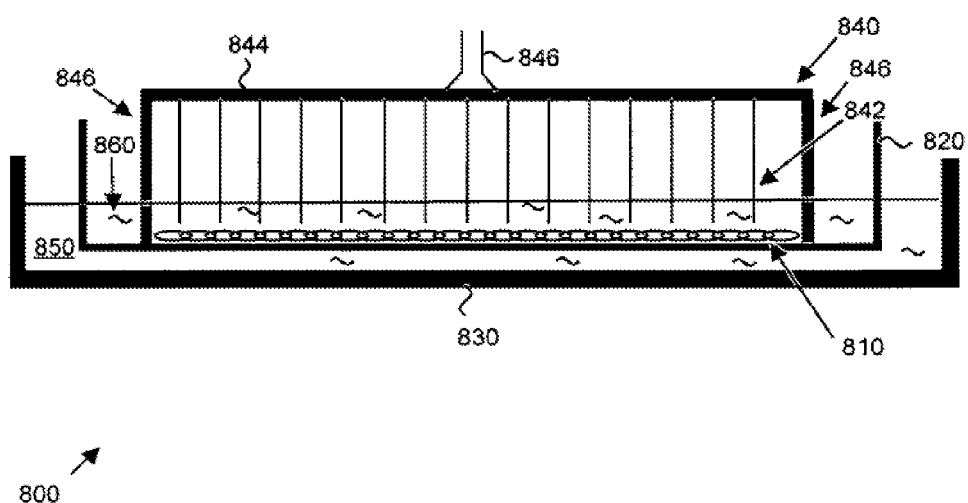

FIG. 8 shows an example of an avalanche apparatus 800 suitable for molecular delivery of agents to adherent cells or tissue according to the present invention. In this arrangement, cells 810 are growing on an adherent surface 820 placed in a nonporous substrate 830, such as a tissue culture plate. Adherent surface 820 may be, for example, a tissue culture insert made of porous material such as polycarbonate. Cells could also be grown directly on nonporous substrate 830. A gelatinous matrix and/or feeder layer may also be present (not shown). A probe 840 with pillar electrodes 842, which serve as avalanche electrodes, surface 844, walls 846, and connection 848 to a voltage source (not shown) is brought into a solution 850 containing agent 860. In the embodiment shown, surface 844 and walls 846 make up a return electrode. Pillar electrodes 842 are positioned a defined distance from cells 810, e.g. about 1 mm. This defined distance is preferably in the range of about 0.5 mm to about 2 cm. Walls 846 may extend beyond the edge of pillar electrodes 842 to support the electrodes at this defined distance. In addition, pillar electrodes 842 are preferably about 0.5 mm to about 2 cm apart.

Avalanche Chamber

Figure 9:
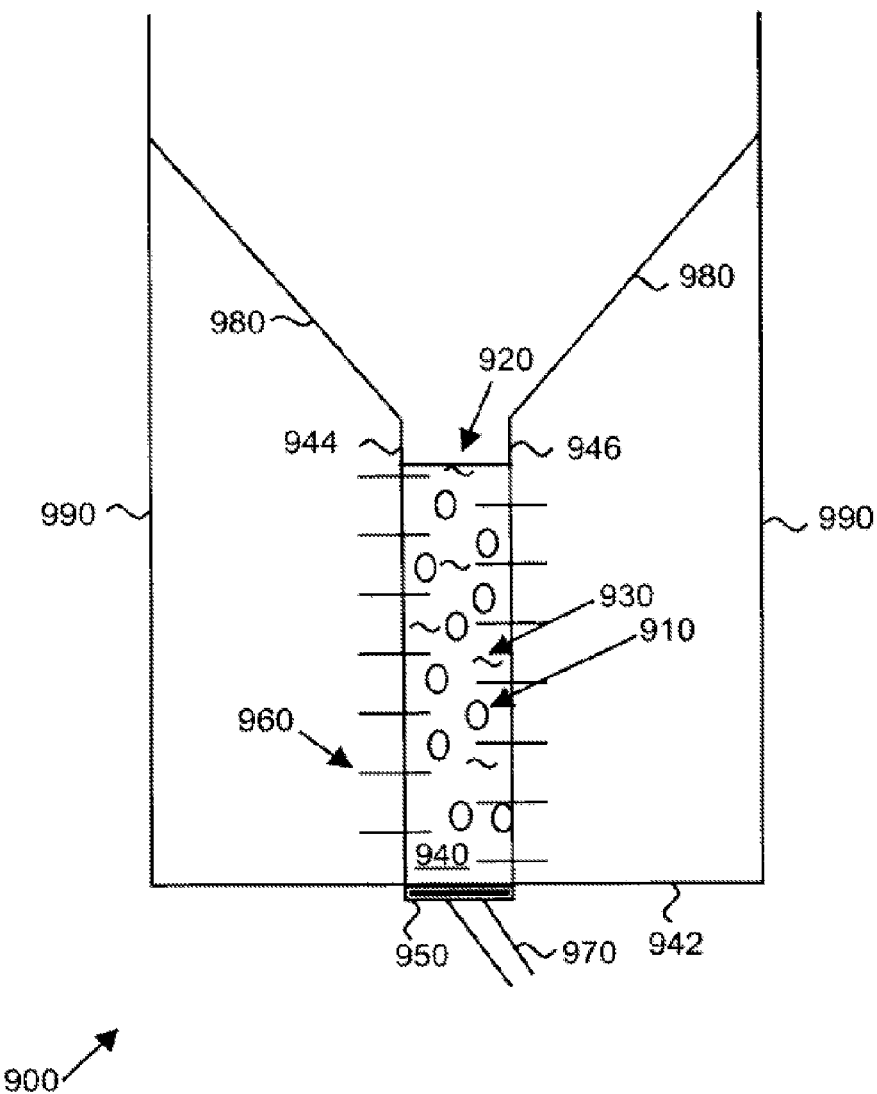

FIG. 9 shows an example of an avalanche apparatus 900 suitable for molecular delivery of agents to cells or tissue in solution according to the present invention. In this arrangement, cells 910 are suspended in solution 920 with agent 930 in chamber 940 with bottom 942 and side walls 944 and 946. Chamber 940 contains return electrode 950, at least one array of avalanche electrodes 960, and connection 970 to a voltage source (not shown). The return electrode 950 may be on bottom 942, as shown, or may be part of one or both of side walls 944 and 946. In addition, arrays of avalanche electrodes 960 may be on both side walls 944 and 966, as shown, or on only one side wall. Preferably, the arrays of avalanche electrodes 960 on side walls 944 and 966 are spatially staggered as shown. Also preferably, the distance between side walls 944 and 966 is between about 0.5 mm and about 2 cm. (The distance between side walls 944 and 966 should be about half this distance if only one array of electrodes is used.) Any type of avalanche electrode may be used according to the present invention, including but not limited to planar electrodes and pillar electrodes. Avalanche electrodes in an array are preferably spaced between about 0.5 mm and about 2 cm apart to provide adequate coverage of the solution volume. Avalanche electrodes 960 could be simultaneously or alternately active. Preferably, chamber 940 also contains angled walls 980, and additional side walls 990, as shown. This allows nutrients and additional fluid to be added to chamber 940 after agent transfer is complete.

Avalanche Apparatus for Tissue

Figure 10:
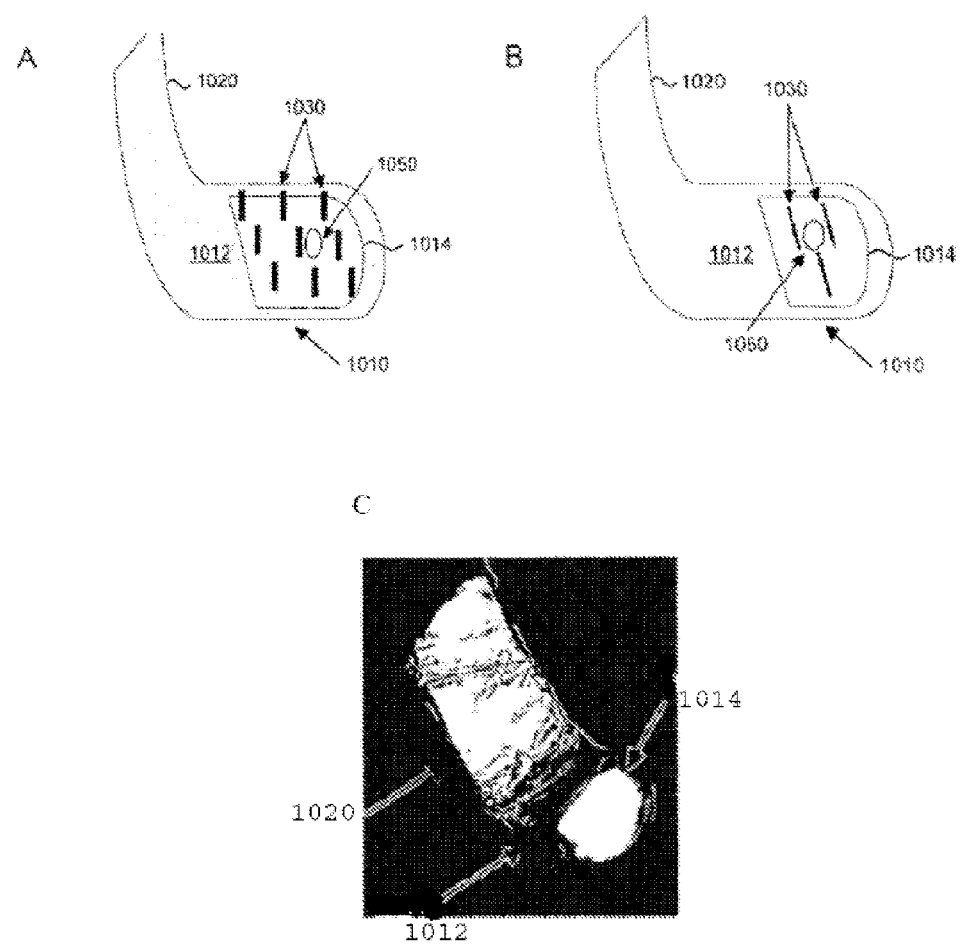

FIG. 10 shows two embodiments of an avalanche apparatus suitable for transfer of agents into tissue in vivo. These apparatuses are particularly well suited for trans-scleral applications. The apparatuses include a surface 1010 and a handle 1020. Surface 1010 preferably includes two regions 1012 and 1014, as shown. Region 1012 serves as the return electrode. Region 1014 is preferably made of an optically clear material, and includes avalanche electrodes 1030. Avalanche electrodes 1030 may protrude from surface region 1014, as shown in FIG. 10A or may be planar to surface region 1014, as shown in FIG. 10B. Surface region 1014 also preferably includes a light probe 1050. Typically, the apparatus would be connected to a voltage source through a wire attached to handle 1020 (not shown). FIG. 10C shows an image of the apparatus shown schematically in FIG. 10B.

Avalanche Apparatus for Skin

Figure 11:
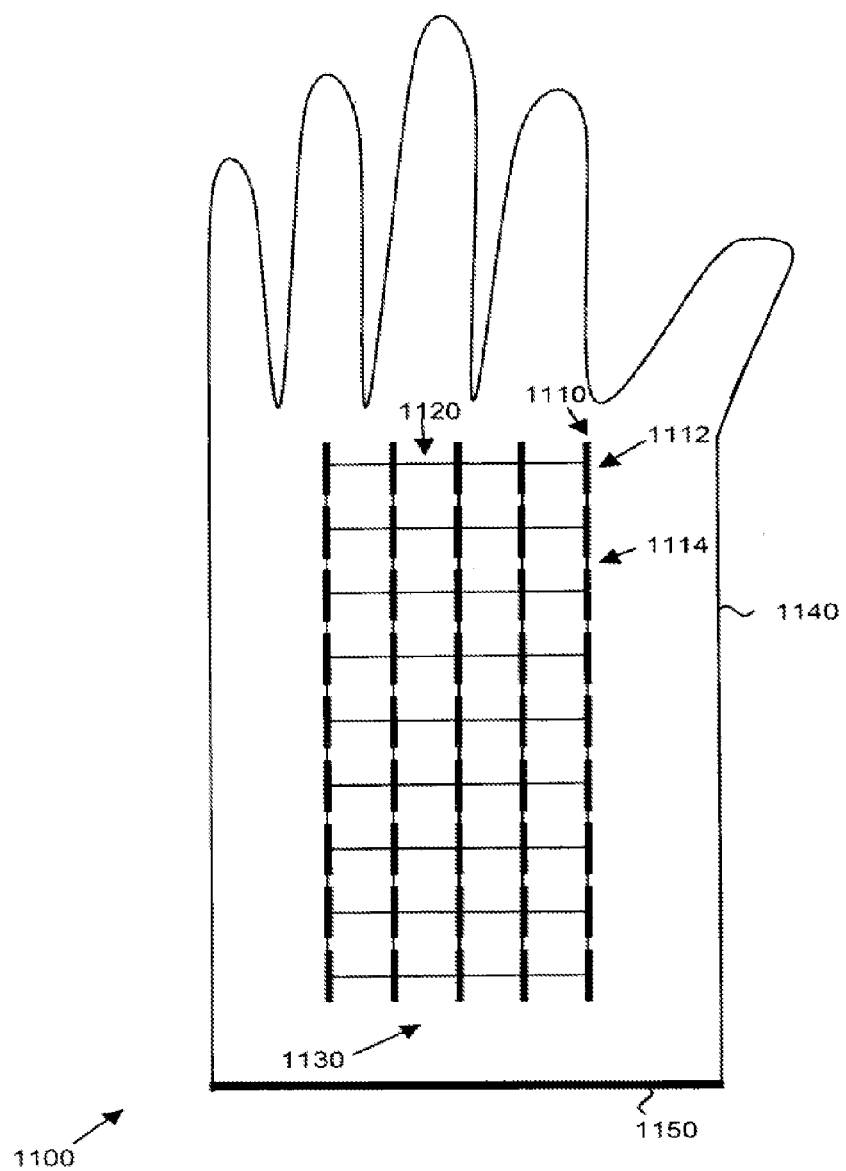

FIG. 11 shows an embodiment of an avalanche apparatus 1100 that may be useful for dermal applications. Apparatus 1100 contains wires 1110 having insulation 1112. Insulation 1112 is removed at regularly spaced intervals 1114 (preferably between about 0.5 mm and 2 cm apart) to expose wires 1110. These exposed regions serve as avalanche electrodes. Wires 1110 are flexibly connected by nonconductive connectors 1120 to form a mesh 1130. Mesh 1130 may in turn be incorporated into a glove 1140, as shown. In one embodiment, glove 1140 contains a return electrode 1150 at its base. Glove 1140 may be connected to a voltage source (not shown) through any means known in the art.

EXAMPLES

Example 1

Comparison of Electron Avalanche Versus Traditional Electroporation in DNA Transfer Because electroporation protocols vary for different tissues, experiments were first conducted to determine the optimal protocol for transfecting chorioallantoic membrane (CAM) from a developing chicken egg using traditional electroporation. CAM is a live, readily available, and inexpensive tissue. Its epithelial layer is uniform and has high resistance, making it a good model for epithelial cell layers, such as retinal pigment epithelium (RPE). In this model system, 100 μg of pNBL2 plasmid DNA encoding the luciferase gene was pipetted onto the CAM, and pulses were applied. Specifically, a 250-μs, 150-V phase, followed by a 5-ms, 5-V phase in the same polarity was applied. Optimal results were achieved with 50 cycles applied at 1 Hz. The tissue was then cultured and assayed for luciferase bioluminescence. Luciferase expression using this method was about $10^4$ photons/s.

Figure 12:
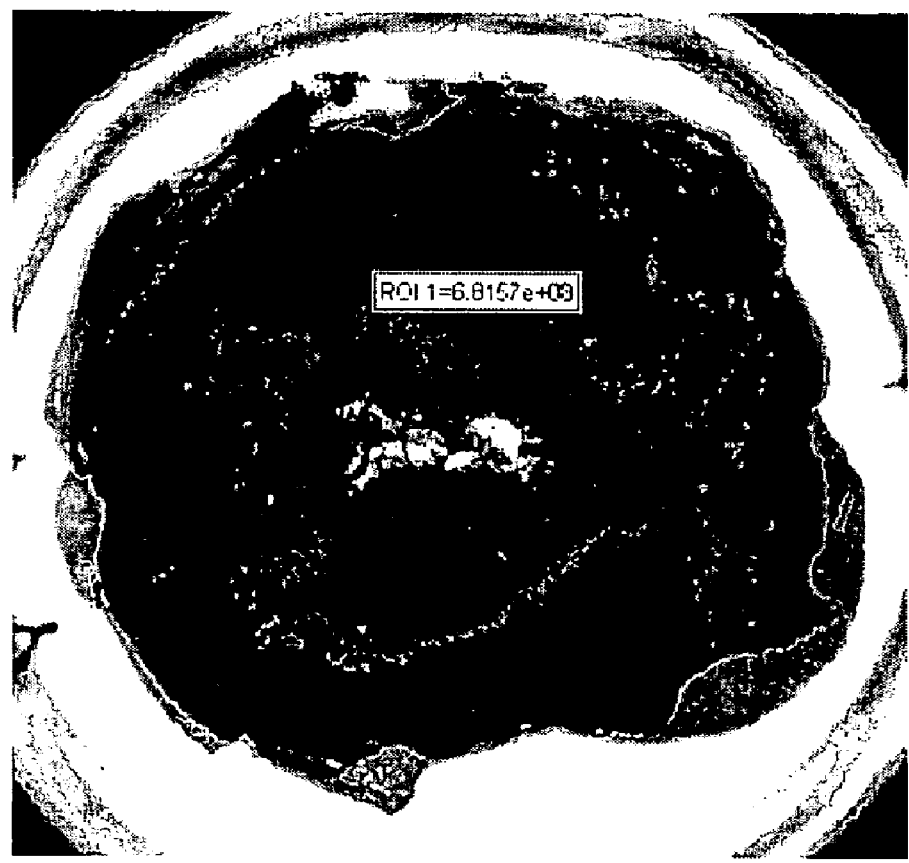
FIGS. 12-15 show examples of DNA transfer using methods and apparatuses according to the present invention.
Figure 13:
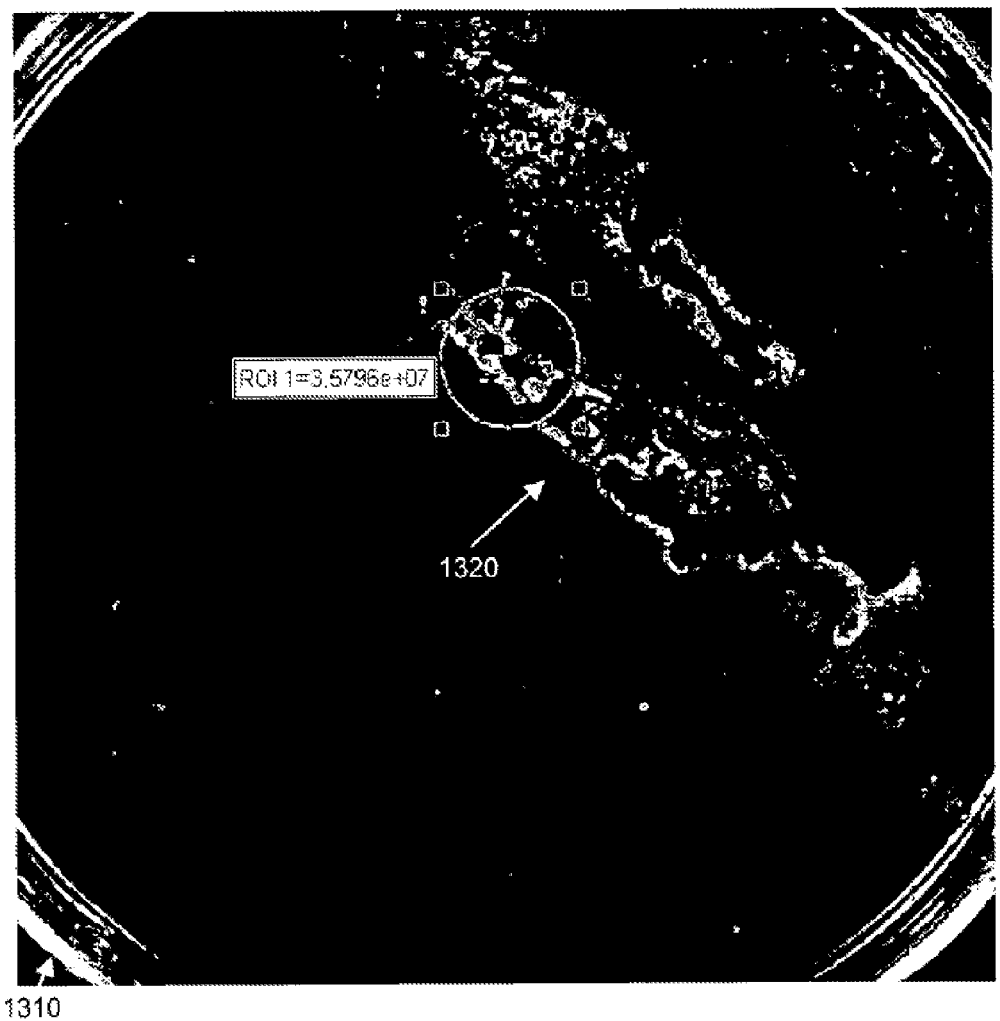

For electron-avalanche transfection, a 50-μm diameter wire microelectrode 1 mm in length was used to apply a series of symmetric biphasic pulses, with each phase 250 μs in duration and 600 V in amplitude. The microelectrode was scanned over a 4-mm² area, and approximately 50 pulses were applied. As shown in FIG. 12, the resultant luciferase expression was about $10^9$ photons/s, 10,000-fold higher than levels seen with conventional electroporation.

Example 2

Spatial Control of Avalanche-mediated Transfection 293 cells were cultured as known in the art in a 10 cm dish 1310, with DMEM plus 3% serum, to confluence. Medium was removed and 2 mL PBS was applied to the 10 cm dish 1310. 100 microliters of DNA was added, where the DNA cassette included the luciferase gene under control of the CMV promoter. An avalanche electrode was used to permeabilize cells in a narrow streak that extended across the plate, and then in a zig-zag pattern. DNA was removed and medium was replaced. Cells were cultured for 24 hours and subjected to bioluminescence imaging (IVIS 200, Xenogen Corp). Signal 1320 is shown by shading, and background is the rest of the plate. This experiment shows that the avalanche method provides excellent spatial control of transfection in situ.

Example 3

Surgical Procedure for RPE Layer Transfection

A probe for trans-scleral electroporation, as shown in FIG. 10, was used to transfect the RPE layer of a rabbit eye. The probe included a nonconductive clear plastic stripe, which was bent at the distal end for better penetration under the conjunctiva. The proximal end was mounted on a handle, which included an electric cable for the avalanche and return electrodes and a light probe for alignment. Wire electrodes of 100 micrometers in diameter were assembled on the concave side of the stripe to be faced towards the sclera. These microelectrodes were arranged as an array to provide wider surface of treatment and surrounded by the return electrode. To avoid muscular contraction due to electric stimulation the electric field should be localized within a volume of the target tissue. For this purpose small active electrodes should be surrounded by the return electrodes. Accordingly, a wide return electrode surrounding the array of active microelectrodes limited the electric field to the proximity of the microelectrode array thus preventing strong muscle contraction. In one implementation the array was a 3×3 array of tungsten microelectrodes, normal to the surface plane and protruding from the plastic surface by about 0.3 mm. Another probe had 3 electrodes 0.5 mm in length, placed in plane with the surface of the probe.

The experimental procedure was as follows. 100 microliters of DNA was injected into the subretinal space with a 30 G needle forming a bleb. The probe was scanned under the sclera in the direction normal to the electrodes in order to treat uniformly the whole area under the bleb. Both probes (i.e., the probes of FIGS. 10A and 10B) gave good transfection efficacy and no visible damage to the RPE and retina. The light source on the probe was used for alignment in proximity to the bleb.

Figure 14:
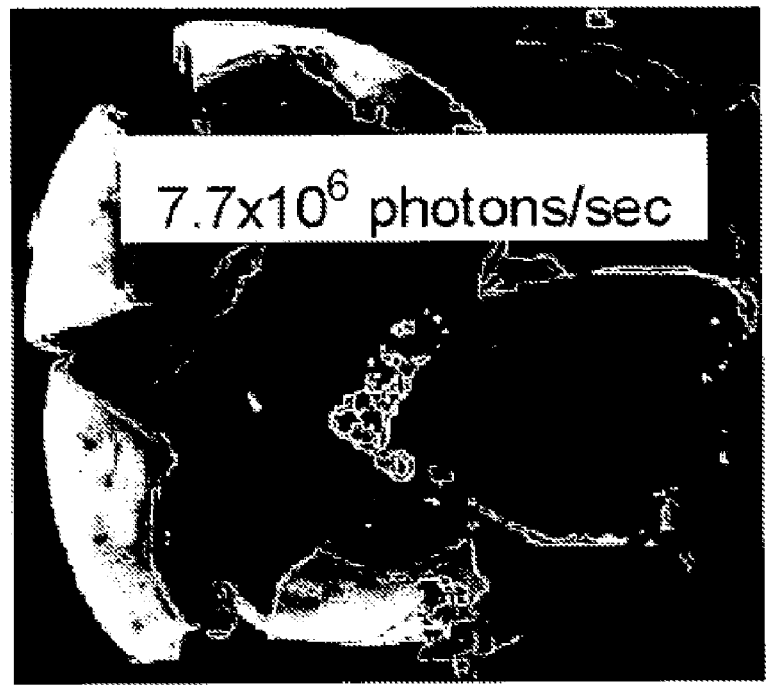
Figure 14:
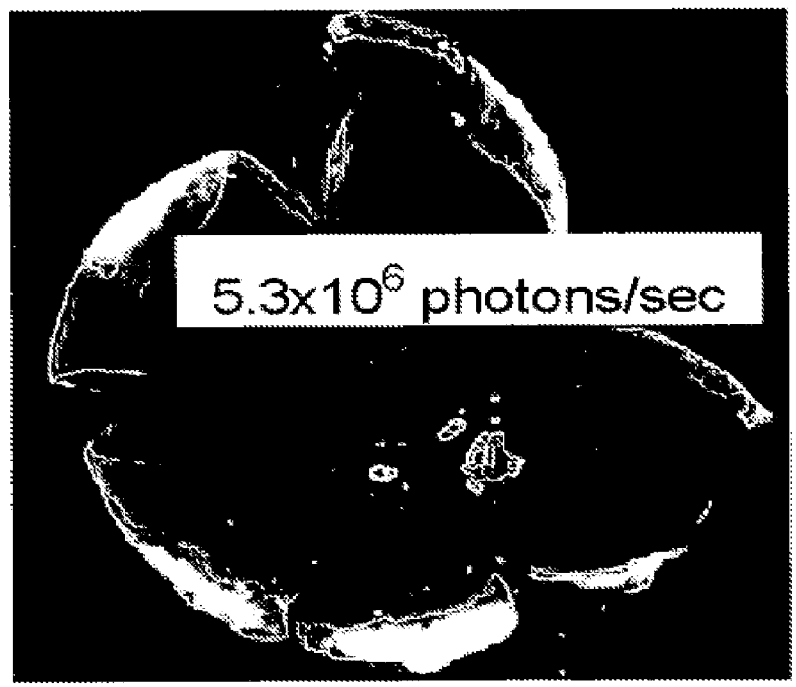

FIG. 14 shows results obtained according to this embodiment of the invention with a probe such as in FIG. 10A (14A) and 10B (14B). The avalanche method resulted in very high efficiency electrotransfection. Furthermore, this technique was effective without any visible damage to RPE and retina, and the retina was reattached and appeared healthy within 24 hours.

Example 4

Transfection of Conjunctival Tissue With Luciferase Gene

A study was conducted in support of the method described herein, where a luciferase marker gene was transfected into conjunctiva tissue. Conjunctival tissue was explanted from adult New Zealand White rabbits and placed in tissue culture dishes. All samples were placed in 1 mL phosphate buffered saline solution with 100 micrograms of plasmid DNA encoding the luciferase gene under a CMV promoter. All samples were cultured in Dulbecco's Modified Eagle Medium (DMEM) plus 10% serum and antibiotic/antimitotic for 24 hours after transfection. Samples were then treated with luciferin substrate (150 micrograms luciferin per ml medium) and imaged using the IVIS-200 system (Xenogen Corp.).

Figure 15:
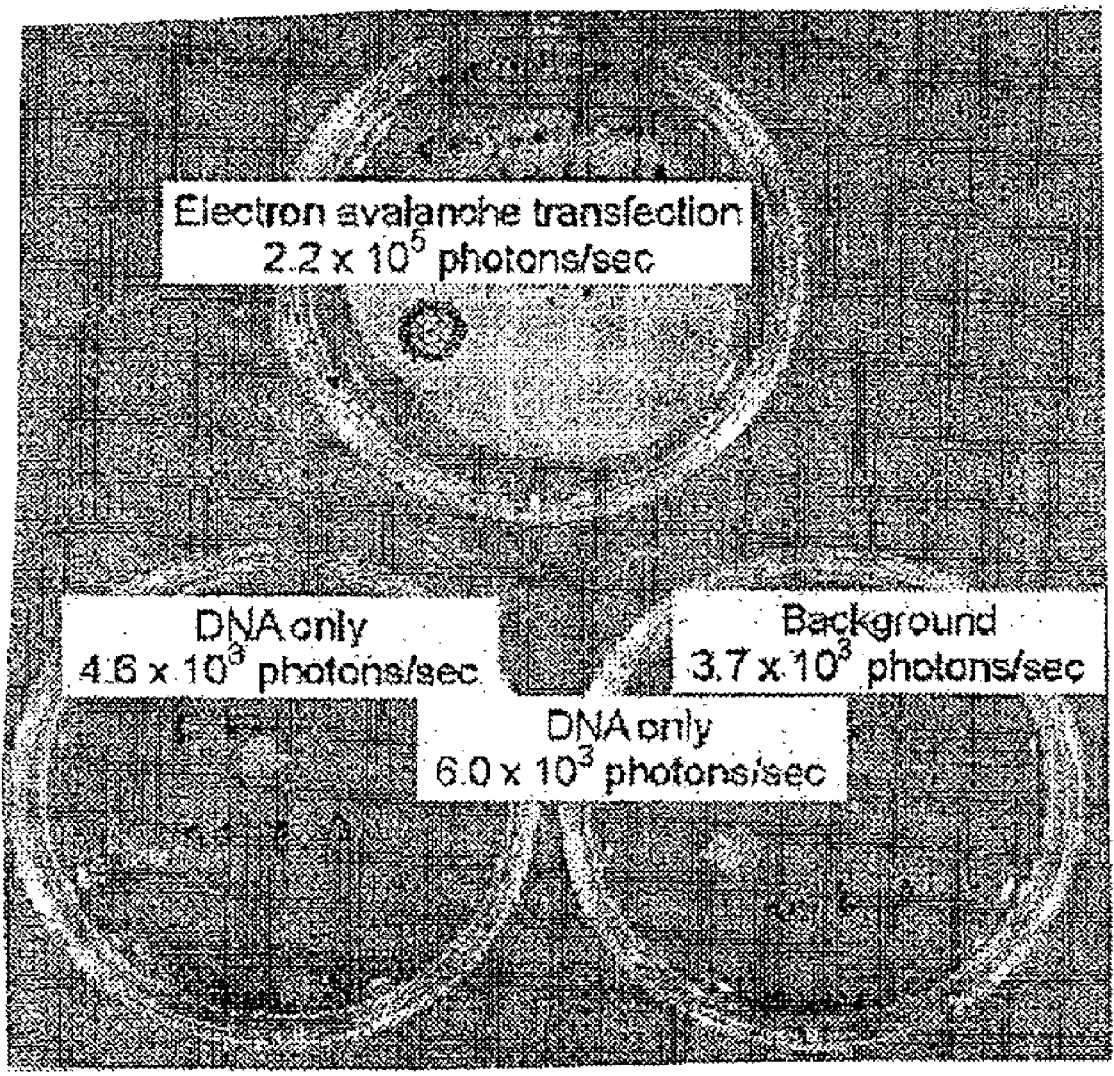

The conjunctival tissue, which contained conjunctival fibroblasts, was transfected using electron-avalanche mediated transfection with a luciferase marker gene. A control sample of tissue was contacted with the luciferase gene in the absence of electron-avalanche mediated transfection. Twenty-four hours after transfection, bioluminescence was measured. As shown in FIG. 15, the tissue transfected with electron-avalanche mediated transfection emitted $2.2\times10^5$ photons/sec, two orders of magnitude higher than the cells transfected in the absence of the electron-avalanche mediated transfection ($4.6\times10^3$ photons/sec). Background emission was measured at $3.7\times10^3$ photons/sec.

As one of ordinary skill in the art will appreciate, various changes, substitutions, and alterations could be made or otherwise implemented without departing from the principles of the present invention. Accordingly, the scope of the invention should be determined by the following claims and their legal equivalents.

The invention claimed is:

1. A method of directly transferring a polypeptide or an RNA molecule into a cell, comprising:
   (a) providing a polypeptide or an RNA molecule outside a cell; and
   (b) generating an electric field and a mechanical stress wave by applying a voltage to an electrode to form a plasma discharge, the electrode providing both the electric field and the mechanical stress wave to the cell, thereby directly transferring the polypeptide or the RNA molecule into the cell.

2. The method of claim 1, wherein the electric field and mechanical stress wave are generated by applying voltage pulses at a frequency of between about 0.1 Hz and about 1 kHz.

3. The method of claim 1, wherein generating the electric field and the mechanical stress wave comprises generating a non-uniform electric field between the electrode and a return electrode, wherein the electric field around the electrode is sufficient for generating a plasma discharge.

4. The method of claim 1, wherein the cell is a eukaryotic cell, a prokaryotic cell, a primary cell, a cell line, or is part of a tissue.

5. The method of claim 1, wherein generating the electric field and the mechanical stress wave permeabilizes the cell.

6. The method of claim 1, wherein generating the electric field and the mechanical stress wave comprises generating the electric field and the mechanical stress wave substantially concurrently.

7. The method of claim 1, wherein the plasma discharge formed is a transient plasma discharge near the cell.

8. The method of claim 2, wherein the cell is a eukaryotic cell, a prokaryotic cell, a primary cell, a cell line, or is part of a tissue.

9. The method of claim 2, wherein generating the electric field and the mechanical stress wave permeabilizes the cell.

10. The method of claim 7, wherein the cell is a eukaryotic cell, a prokaryotic cell, a primary cell, a cell line, or is part of a tissue.

11. The method of claim 7, wherein forming the transient plasma discharge permeabilizes the cell.

12. A method of transferring a polypeptide or an RNA molecule into a cell, comprising:
    (a) providing a polypeptide or an RNA molecule outside a cell; and
    (b) generating an electric field and a mechanical stress wave by applying a voltage in a range of about 100 V to about 10 kV to an electrode to form a plasma discharge, the electrode providing both the electric field and the mechanical stress wave to the cell, thereby transferring the polypeptide or the RNA molecule into the cell.

13. The method of claim 1, wherein the electrode is positioned at a distance of about 0.01 mm to about 1 cm from the cell.

14. The method of claim 2, wherein the voltage is applied in a range of about 100 V to about 10 kV.

15. The method of claim 2, wherein the electrode is positioned at a distance of about 0.01 mm to about 1 cm from the cell.

16. The method of claim 12, wherein the plasma discharge formed is a transient plasma discharge near the cell.

17. A method of transferring a polypeptide or an RNA molecule into a cell, comprising:
    (a) providing the polypeptide or the RNA molecule outside of the cell; and
    (b) transferring the polypeptide or the RNA molecule into the cell by applying voltage to an electrode to form a transient plasma discharge near the cell, wherein the electrode is positioned at a distance of about 0.01 mm to about 1 cm from the cell, the electrode providing both an electric field and a mechanical stress wave to the cell.

* * * * *